United States Patent [19]

Nüsslein et al.

[11] 4,225,338

[45] Sep. 30, 1980

[54] UREA DERIVATIVES, PROCESS FOR MAKING THE SAME AND HERBICIDAL COMPOSITION CONTAINING THE SAME

[75] Inventors: Ludwig Nüsslein; Friedrich Arndt, both of Berlin, Fed. Rep. of Germany

[73] Assignee: Schering A G, Berlin and Bergkamen, Fed. Rep. of Germany

[21] Appl. No.: 941,302

[22] Filed: Sep. 11, 1978

Related U.S. Application Data

[63] Continuation of Ser. No. 730,715, Oct. 8, 1976, abandoned.

[30] Foreign Application Priority Data

Dec. 19, 1975 [DE] Fed. Rep. of Germany ....... 2558078

[51] Int. Cl.$^3$ .................... A01N 47/30; C07C 127/00
[52] U.S. Cl. .......................................... 71/120; 71/98; 71/103; 71/105; 71/76; 260/465 D; 260/553 A
[58] Field of Search ................ 71/120, 98; 260/553 A

[56] References Cited

U.S. PATENT DOCUMENTS

| | | | |
|---|---|---|---|
| 2,726,150 | 12/1955 | Wolter | 71/120 |
| 3,241,942 | 3/1966 | Martin et al. | 71/120 |
| 3,244,504 | 4/1966 | Martin et al. | 71/120 |
| 3,488,182 | 1/1970 | Ebner | 71/120 |
| 3,520,925 | 7/1970 | Koenig et al. | 71/120 |
| 3,734,961 | 5/1973 | Englehart | 71/120 |
| 3,790,364 | 2/1974 | Teach | 71/120 |
| 3,895,061 | 7/1975 | Richter | 71/120 |
| 3,903,154 | 9/1975 | Singer | 71/119 |

OTHER PUBLICATIONS

Settepani et al., "Preparation of 1,3-diaryl, etc." (1973), CA 79 No. 126391c, (1973).
Lackenbaugh, "2-Phenylimino-3-alkyloxazolidines, etc." (1959), CA 54 p. 811 (1960).
Deilstein, "N-cyclopropyl-n'-phenyl-barnestoff" Beilstein, vol. 12, p. 350, Syst. No. 1627 (1929).

*Primary Examiner*—Glennon H. Hollrah
*Attorney, Agent, or Firm*—Michael J. Striker

[57] ABSTRACT

A urea derivative of the formula $$\begin{array}{c} H_2C \\ | \\ H_2C \end{array} \!\!\! \diagdown \!\!\! \begin{array}{c} \\ CH-NH-CO-N-R_1 \\ | \\ R \end{array}$$

in which
R is hydrogen, alkyl, alkenyl, cyanoalkyl or phenyl and
$R_1$ is

[benzene ring with $X_n$ substituent]

X, if several, being the same or different and X being hydrogen, alkyl, alkoxy, halogenoalkyl, alkylthio, alkylsulfinyl, alkylsulfonyl, halogeno or nitro, and n being an integer from 1 to 3. The compounds are useful as reactive agents in herbicidal composition. The invention also concerns a herbicidal composition in which a compound of the invention is the active agent or one of the active agents.

5 Claims, No Drawings

UREA DERIVATIVES, PROCESS FOR MAKING THE SAME AND HERBICIDAL COMPOSITION CONTAINING THE SAME

This is a continuation of application Ser. No. 730,715, filed Oct. 8, 1976, now abandoned.

BACKGROUND OF THE INVENTION

The invention relates to urea derivatives, herbicidal compositions containing the same as active agents or as one of the active agents and a process for making the compounds.

Urea derivatives with herbicidal action have been disclosed previously, U.S. Pat. No. 3,228,762 and Swiss Pat. No. 466,943. These compounds, however, have normally only slight selective properties.

It is therefore an object of the present invention to provide for herbicidal agents which avoid the shortcomings of the prior art agents and in particular have a strong herbicidal action together with a high selectivity.

SUMMARY OF THE INVENTION

This object is met by a urea derivative of the formula $$\begin{array}{c} H_2C \\ | \\ | \\ H_2C \end{array} \Big\rangle CH-NH-CO-N \begin{array}{c} R^1 \\ | \\ R \end{array}$$

wherein R is hydrogen or an aliphatic hydrocarbon residue which may also be substituted or an aliphatic or aromatic hydrocarbon residue which may be interrupted by one or more oxygen atoms and wherein $R_1$ is an unsubstituted or substituted phenyl group.

PREFERRED EMBODIMENTS

Among the compounds just defined excellent herbicidal and selective properties are found in those in which R in the above general formula is hydrogen, alkyl, alkenyl, cyanoalkyl or phenyl and $R_1$ in the above formula is the group $$-\phantom{}\!\!\bigcirc\!\!-X_n$$

wherein X, if several, may be the same or different, and wherein X is hydrogen, alkyl, alkoxy, halogeno alkyl, alkyl-thio, alkylsulfinyl, alkylsulfonyl, halogeno or nitro, and wherein n is from 1 to 3.

The preferred compounds of the invention are those where in the general formula R is hydrogen, $C_1$ to $C_4$ alkyl, alkenyl or phenyl, and R' has the formula just given wherein X is the same or different and is hydrogen, alkyl of 1 to 4 carbon atoms, alkoxy of 1 to 2 carbon atoms, halogeno, trifluoromethyl, methylthio or nitro, n having the meaning as above given.

METHOD OF USE AND DESCRIPTION OF COMPOSITIONS

The urea derivatives of the invention are eminently suited for use against highly resistant monocotyledonous and dicotyledonous weeds, such as *Stellaria media, Senecio vulgaris, Matricaria chamomilla, Lamium amplexicaule, Centaurea cyanus, Amarantus retroflexus, Galium aparine, Chrysanthemum segetum, Ipomoea purpurea, Polygonum lapathifolium, Avena fatua, Alopecurus myosuroides, Echinochloa crus galli, Setaria italica, Digitaria sanguinalis, Sorghum halepense* or *Poa anua*.

The excellent selectively herbicidal properties appear in the use for agricultural crops as for instance in use with sugar beets, common forage alfalfa (Medicato sativa), bush beans, cotton, peanuts, soybeans, potatoes, peas, grains and sugar cane. The compounds also have an action as defoliants and desiccants. The amounts used for application are 0.5 to 5 kg of active agent per hectare (1 hectare being 2.47 acres.) The compounds of the invention can be used either individually or in mixture with each other or with other active agents. Depending on the particular objective it is also possible to add other defoliants, plant protective agents or pesticides.

An improvement of the activity and of the speed of action can be obtained by additives such as organic solvents, cross-linking agents and oils. This would then permit a reduction of the amount employed of the active agent of the invention.

The compounds of the invention or mixtures thereof are normally applied in the form of compositions forming powders, spreading compositions, granulates, solutions, emulsions or suspensions. For this purpose there may be added liquid and/or solid carrier materials or diluents and possibly cross-linking, adhesion, emulsion and/or dispersion promoting agents.

Suitable liquid carrier materials are water, aliphatic and aromatic hydrocarbons and derivatives, such as benzene, toluene, xylene, cyclohexanone, isophorone, dimethylsulfoxide, dimethylformamide and also mineral oil fractions.

As solid carriers there can be used minerals or earths, for instance tonsil, silica gel, talc, kaolin, atta pulgite clay, limestone, silicic acid and plant products, such as flour.

As surface active agents there can be added for instance calciumlignosulfonates, polyoxyethylene-alkylphenolether, naphthalenesulfone acids and their salts, phenolsulfone acids and their salts, formaldehyde condensates, fatty alcoholsulfates as well as substituted benzenesulfone acids and their salts.

The amount of the active agent or agents in the different compositions can be varied within a broad range. The compositions may for instance contain between about 10 to 80% by weight of active agents, about 90 to 20% by weight of liquid or solid carrier materials and, if desired, up to 20% by weight of surface active agents.

The application of the compounds or compositions can be carried out in conventional manner. For instance water can be used as the carrier in sprays of about 100 to 1000 liter per about 2.5 acres. The compounds can be used in the so-called "low volume" as well as in the "ultra-low-volume" applications and they can also be applied in the form of so-called microgranulates.

METHOD OF MAKING

The urea derivatives of the invention have not been described heretofore. They can be made for instance by reacting cyclopropylamine with carbamic acid halides, carbamic acid esters or isocyanates or also by reacting amines with cyclopropylisocyanate, cyclopropylcarbamic acid chloride or carbamic acid esters.

The compounds of the invention can for instance be made by one of the following processes:

I. Cyclopropylamine of the formula

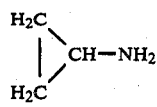

is reacted with
(a) carbamic acid halides of the general formula $$R_1-N-CO-Hal$$
$$\phantom{R_1-N}|\phantom{-CO-Hal}$$
$$\phantom{R_1-}R$$

(b) carbamic acid esters of the general formula $$R_1-N-CO-Y-R_2$$
$$\phantom{R_1-N}|$$
$$\phantom{R_1-}R$$

or
(c) in the case where R in the final compound is intended to be hydrogen, with isocyanates of the general formula $$R_1-N=C=O.$$

The reaction may be carried out upon use of a solvent and in the presence of an acid acceptor;

II. Anilines of the general formula $$R_1-NH-R$$

may be reacted with
(a) cyclopropylisocyanate of the formula

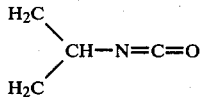

(b) cyclopropylcarbamic acid chloride of the formula

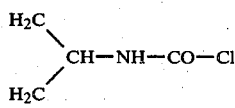

or
(c) cyclopropylcarbamic acid esters of the general formula

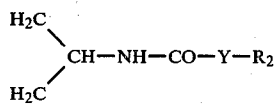

in which case the reaction may again take place upon use of a solvent and in the presence of an acid acceptor.

In all these formulas R and $R_1$ have the same meaning as in the above formula of the final urea derivative, provided that at least one of these two groups must be phenyl in the amiline formula, $R_2$ is alkyl or phenyl, Y is oxygen or sulphur and Hal is halogen.

The cyclopropylisocyanate that is used in the reaction IIa can be obtained by direct phosgenizing of cyclopropylamine hydrochloride at an elevated temperature such as from 80° to 150° C. in an inert solvent or by pyrolysis of 1-cyclopropyl-3,3-diphenylurea.

For instance 100 g of the cyclopropyldiphenylurea may be subjected to pyrolysis at temperatures in excess of 250° C. There are then obtained 21.8 g of cyclopropylisocyanate (66% of the theoretical amount). The boiling point of the redistilled compound at 772 torr is 88° C.

Other processes for making the cyclopropylisocyanate involve the conversion of derivatives of the cyclopropanoic acid, such as, the degradation of the propanoic acid amide by the method of A. W. Hofmann or the thermic decomposition of cyclopropane carbhydroxamic acid by the method of W. Lossen.

In those processes where hydrogen halide acids are formed an acid acceptor is added to the reaction in the form of an organic base such as a tertiary amine, for instance triethylamine or dimethylaniline, a pyridine base or suitable inorganic bases such as the oxides, hydroxides or carbonates of the alkali or earth alkali metals.

The reaction is carried out at temperatures between $-20°$ C. and 120° C., usually at room temperature. Useful reaction media are solvents which are inert against the compounds of the reaction. As such the following may be used:

(a) Aliphatic and aromatic hydrocarbons, such as petroleum ether, cyclohexane, benzene, toluene and xylene, (b) halogenated hydrocarbons, such as methylene chloride, chloroform, carbontetrachloride and halogenated ethylenes, (c) ether type compounds such as diethylether, diisopropylether, tetrahydrofuran and dioxan, (d) ketones, such as acetone, methylisobutylketone and isophorone, (e) esters such as acetic acid methyl-and ethyl ester, (f) acid amides such as dimethylsulfformamide and hexamethylphosphoric acid triamide, (g) carboxylic acid nitriles such as acetonitrile and many others.

The following examples further illustrate the making of the compounds of the invention.

EXAMPLE A 1-cyclopropyl-3-(3,5-dimethylphenyl)-urea 14.7 g of 3,5-dimethylphenylisocyanate were slowly added by a dropper upon stirring at a temperature of 28° C. to a solution of 5.7 g of cyclopropylamine in 200 ml diisopropylether. The formed precipitate was removed by suction after an hour, was washed with a small amount of diisopropylene and finally dried. There were thus obtained 18.9 g of 1-cyclopropyl-3-(3,5-dimethylphenyl)-urea (92.5% of the theoretical value) having a melting point of 169° C.

EXAMPLE B 1-cyclopropyl-3,3-diphenylurea 200 g phosgene were condensed at $-20°$ C. and diluted with 500 ml toluene. A solution of 338.4 g diphenylamine and 202 g triethylamine in 1 liter toluene was then added dropwise upon stirring at a temperature between 0° and 5° C. and the reaction temperature was permitted to rise to room temperature.

After standing overnight the mixture was three times stirred into ice water (300 ml) and the organic phase was dried on magnesium sulfate.

The thus formed solution of diphenylcarbamic acid chloride was then added dropwise upon stirring to a mixture of 114 g of cyclopropylamine, 202 g of triethylamine and 500 ml of toluene. During the addition the temperature inside the flask rose to 85° C. Subsequently the reaction mass was heated to boiling point for 15 minutes and then cooled. The precipitated triethylammoniumchloride was removed by suction and the solvent was distilled off in a vacuum. The remaining residue was subjected to recrystallization from diisopropylether. The yield in 1-cyclopropyl-3,3-diphenylurea was 440.2 g (87.2% of the theoretical value). The melting point was 98° C.

EXAMPLE C

1-cyclopropyl-3-(4-fluorophenyl)-urea 8.4 ml of cyclopropylisocyanate were added dropwise upon stirring at room temperature to a solution of 11.1 g of 4-fluoroaniline in 100 ml diisopropylether. There then formed 1-cyclopropyl-3-(4-fluorophenyl)-urea as precipitate. It was removed by suction and subsequently washed with diisopropylether and dried. The yield was 18.8 g (96.8% of the theoretical value). The melting point was 205° C.

In an analogous manner the following urea derivatives were made:

| Compound | Physical constants (m.p.,acid density) |
|---|---|
| 1-cyclopropyl-3-(3-nitrophenyl)-urea | 147° C. |
| 1-cyclopropyl-3-(3-methoxyphenyl)-urea | 113° C. |
| 1-(3-bromophenyl)-3-cyclopropyl-urea | 143° C. |
| 1-cyclopropyl-3-(3-fluorophenyl)-urea | 126° C. |
| 1-cyclopropyl-3-methyl-3-phenyl-urea | $n_D^{20}$ 1,5549 |
| 1-(2-chlorophenyl)-3-cyclopropyl-urea | 132° C. |
| 1-(3-chloro-4-methylphenyl)-3-cyclopropylurea | 186° C. |
| 1-cyclopropyl-3-(4-methylphenyl)-urea | 150° C. |
| 1-cyclopropyl-3-phenylurea | 164° C. |
| 1-cyclopropyl-3-(4-chlorophenyl)-urea | 222° C. |
| 1-cyclopropyl-3-(3,4-dichlorophenyl)-urea | 209° C. |
| 1-cyclopropyl-3-(3-methylphenyl)-urea | 122° C. |
| 1-cyclopropyl-3-(2-methylphenyl)-urea | 146° C. |
| 1-(4-chloro-2-methylphenyl)-3-cyclopropylurea | 215° C. |
| 1-(3-chlorophenyl)-3-cyclopropyl-urea | 131° C. |
| 1-cyclopropyl-3-(3-trifluoromethylphenyl)-urea | 141° C. |
| 1-cyclopropyl-3-(3,4-dimethylphenyl)-urea | 181° C. |
| 1-cyclopropyl-3-(2,3-dimethylphenyl)-urea | 190° C. |
| 1-cyclopropyl-3-(2,4-dimethylphenyl)-urea | 187° C. |
| 1-cyclopropyl-3-(2,6-dimethylphenyl)-urea | 222° C. |
| 1-(4-bromophenyl)-3-cyclopropyl-urea | 213° C. |
| 1-cyclopropyl-3-(4-methoxyphenyl)-urea | 150° C. |
| 1-cyclopropyl-3-(3-methoxy-4-methylphenyl)-urea | 177° C. |
| 1-(3-ethoxyphenyl)-3-cyclopropyl-urea | 127° C. |
| 1-(4-ethoxyphenyl)-3-cyclopropyl-urea | 163° C. |
| 1-(3-bromo-4-iodophenyl)-3-cyclopropyl-urea | 225° C. |
| 1-cyclopropyl-3-methyl-3-(3-methyl-phenyl)-urea | 70° C. |
| 1-ethyl-1-(3-chlorophenyl)-3-cyclopropylurea | 68° C. |
| 3-ethyl-1-cyclopropyl-3-phenyl-urea | 79° C. |
| 1-ethyl-3-cyclopropyl-1-(3-methylphenyl)-urea | 58° C. |
| 1-cyclopropyl-3-(4-methylthiophenyl)-urea | 165° C. |
| 1-cyclopropyl-3-(4-nitrophenyl)-urea | 192° C. |
| 1-(4-chloro-3-nitrophenyl)-3-cyclopropylurea | 168° C. |
| 1-butyl-3-cyclopropyl-1-phenyl-urea | $n_D^{20}$ 1,5320 |
| 1-allyl-3-cyclopropyl-1-phenyl-urea | $n_D^{20}$ 1,5548 |
| 1-(4-butylphenyl)-3-cyclopropyl-urea | 120° C. |
| 1-(3-chloro-6-methylphenyl)-3-cyclopropylurea | 158° C. |
| 1-(2-ethylphenyl)-3-cyclopropyl-urea | 154° C. |
| 1-ethyl-3-cyclopropyl-1-(4-methylphenyl)-urea | 86° C. |
| 1-butyl-1-(3-chlorophenyl)-3-cyclopropylurea | $n_D^{20}$ 1,5421 |
| 1-sec.-butyl-3-cyclopropyl-1-phenylurea | 46° C. |
| 1-cyclopropyl-3-methyl-3-(4-methylphenyl)-urea | $n_D^{20}$ 1,5590 |
| 1-(4-chloro-2,5-dimethoxyphenyl)-3-cyclopropylurea | 143° C. |
| 1-cyclopropyl-3-phenyl-3-propyl-urea | 50° C. |
| 1-cyclopropyl-3-isopropyl-3-phenyl-urea | 110° C. |
| 1-cyclopropyl-3-isobutyl-3-(3-methylphenyl)-urea | 48° C. |
| 1-cyclopropyl-3-isobutyl-3-phenyl-urea | 54° C. |
| 1-ethyl-1-(4-chlorophenyl)-3-cyclopropylurea | 95° C. |
| 1-(3-ethylphenyl)-1-butyl-3-cyclopropyl-urea | $n_D^{20}$ 1,5320 |
| 1-(3-chlorophenyl)-3-cyclopropyl-1-methyl-urea | $n_D^{20}$ 1,5721 |
| 1-cyclopropyl-3-(4-isopropylphenyl)-urea | 154° C. |
| 1-(2-chloroethyl)-3-cyclopropyl-1-phenyl-urea | 73° C. |
| 1-(3-chlorophenyl)-1-cyanomethyl-3-cyclopropyl-urea | 107° C. |
| 1-cyanomethyl-3-cyclopropyl-1-(3-trifluoro-methylphenyl)-urea | 102° C. |
| 1-cyanomethyl-3-cyclopropyl-1-phenyl-urea | 112° C. |

The compounds of the invention are colorless and non-smelling, oily or crystalline materials. They are only slightly soluble in water but have good solubility in organic solvents such as hydrocarbons, halogenated hydrocarbons, ethers, ketones, alcohols, carboxylic acids, esters, carboxylic acid amides and carboxylic acid nitriles.

ACTIVITY

The following examples will further illustrate the activity of the urea derivatives of the invention:

EXAMPLE 1

Sinapis and solanum were sprayed as test plants in a preemergence and a postemergence application with the compounds of the invention listed in the table below. The compounds were employed in an amount of 5 kg of active agent per about 2.5 acres suspended in 500 liter of water per the same area. Three weeks after treatment the results were evaluated on a scale from 0=no effect to 4=total destruction of the plants. As appears from the table that follows in most cases the test plants were subject to destruction.

TABLE I

| Compound of invention | preemergence mustard sinapis | preemergence tomato solanum | postemergence mustard sinapis | postemergence tomato solanum |
|---|---|---|---|---|
| 1-cyclopropyl-3-methyl-3-phenyl-urea | 4 | 4 | 4 | 4 |
| 1-(2-chlorophenyl)-3-cyclopropyl-urea | 4 | 4 | 4 | 4 |
| 1-(3-chloro-4-methylphenyl)-3-cyclopropylurea | 4 | 4 | 4 | 4 |
| 1-cyclopropyl-3-(4-methylphenyl)-urea | 4 | 4 | 4 | 4 |
| 1-cyclopropyl-3-(3,4-dichlorophenyl)-urea | 4 | 4 | 4 | 4 |
| 1-cyclopropyl-3-(4-chlorophenyl)-urea | 4 | 4 | 4 | 4 |
| 1-cyclopropyl-3-phenyl-urea | 4 | 4 | 4 | 4 |
| 1-cyclopropyl-3-(3-methylphenyl)-urea | 4 | 4 | 4 | 4 |
| 1-cyclopropyl-3-(2-methylphenyl)-urea | 4 | 4 | 4 | 4 |
| 1-cyclopropyl-3-(3-trifluoromethylphenyl)-urea | 4 | 4 | 4 | 4 |
| 1-cyclopropyl-3-(3,4-dimethylphenyl)-urea | 4 | 4 | 4 | 4 |
| 1-cyclopropyl-3-(3,5-dimethylphenyl)-urea | 4 | 4 | 4 | 4 |
| 1-cyclopropyl-3-(2,3-dimethylphenyl)-urea | 4 | 4 | 4 | 4 |
| 1-(3-bromo-4-iodophenyl)-3-cyclopropyl-urea | 0 | 0 | 3 | 4 |
| 1-cyclopropyl-3-methyl-3-(3-methylphenyl)-urea | 4 | 4 | 4 | 4 |
| 1-ethyl-1-(3-chlorophenyl)-3-cyclopropyl-urea | 4 | 4 | 4 | 4 |
| 3-ethyl-1-cyclopropyl-3-phenyl)-urea | 4 | 4 | 4 | 4 |
| 1-ethyl-3-cyclopropyl-1-(3-methylphenyl)-urea | 4 | 4 | 4 | 4 |
| 1-cyclopropyl-3-(4-methylthiophenyl)-urea | 0 | 0 | 1 | 0 |
| 1-cyclopropyl-3-(4-nitrophenyl)-urea | 0 | 1 | 0 | 0 |
| 1-(4-chloro-3-nitrophenyl)-3-cyclopropyl)-urea | 0 | 0 | 1 | 4 |
| 1-butyl-3-cyclopropyl-1-phenyl-urea | 4 | 4 | 1 | 1 |
| 1-allyl-3-cyclopropyl-1-phenylurea | 3 | 4 | 4 | 4 |
| 1-(4-butylphenyl)-3-cyclopropylurea | 0 | 0 | 3 | 4 |
| 1-(3-chloro-6-methylphenyl)-3-cyclopropyo-urea | 4 | 4 | 4 | 4 |
| 1-(2-ethylphenyl)-3-cyclopropyl-urea | 4 | 4 | 4 | 4 |
| 1-ethyl-3-cyclopropyl-1-(4-methylphenyl)-urea | 4 | 4 | 4 | 4 |
| 1-butyl-1-(3-chlorophenyl)-3-cyclopropyl-urea | 4 | 4 | 4 | 4 |
| 1-sec.-butyl-3-cyclopropyl-1-phenyl-urea | 4 | 4 | 4 | 4 |
| 1-cyclopropyl-3-methyl-3-(4-methylphenyl)-urea | 4 | 4 | 4 | 4 |
| 1-cyclopropyl-3-phenyl-3-propyl-urea | 4 | 4 | 4 | 4 |
| 1-cyclopropyl-3-isopropyl-3-phenyl-urea | 4 | 4 | 4 | 4 |
| 1-cyclopropyl-3-isobutyl-3-(3-methylphenyl)-urea | 4 | 4 | 4 | 4 |
| 1-cyclopropyl-3-isobutyl-3-phenyl-urea | 4 | 4 | 4 | 4 |
| 1-ethyl-1-(4-chlorophenyl)-3-cyclopropyl-urea | 4 | 4 | 4 | 4 |
| 1-(3-ethylphenyl)-1-butyl-3-cyclopropyl-urea | 4 | 4 | 4 | 4 |
| 1-(3-chlorophenyl)-3-cyclopropyl-1-methyl-urea | 4 | 4 | 4 | 4 |
| 1-cyclopropyl-3-(4-isopropylphenyl)-urea | 4 | 4 | 4 | 4 |
| 1-(3-chlorophenyl)-1-cyanomethyl-3-cyclopropyl-urea | 4 | 4 | 4 | 4 |
| 1-cyanomethyl-3-cyclopropyl-1-(3-trifluoro-methylphenyl)-urea | 4 | 3 | — | — |
| 1-cyanomethyl-3-cyclopropyl-1-phenyl-urea | 4 | 4 | 4 | 4 |

EXAMPLE 2

The plants listed below in Table II were sprayed in a hothouse in a preemergence application with the compounds listed in amounts of 1 kg of active agent per about 2.5 acres. The agents for this purpose were applied in a uniform manner to the ground in the form of aqueous suspensions in amounts of 500 liter per 2.5 acres.

The results found after 3 weeks following the application show that the compounds of the invention are of higher activity and greater selectivity than the control compounds. The evaluation was on a scale from 0=total destruction to 10=plants not injured.

TABLE II

| Compounds of invention | Beet sugar | Bush bean | Wheat | Maize (Indian corn) | Common forage alfalfa | Echinochloa | Setaria | Poa | Digitaria | Avena | Galium | Amarantus | Lamium |
|---|---|---|---|---|---|---|---|---|---|---|---|---|---|
| 1-cyclopropyl-3-phenylurea | 9 | 10 | 10 | 10 | 10 | 0 | 0 | 0 | 0 | 0 | 2 | 0 | 0 |
| Control compound | | | | | | | | | | | | | |
| N-(3-chloro-4-methylphenyl)-N',N'-dimethyl-urea | 0 | 1 | 8 | 7 | 1 | 3 | 1 | 0 | 6 | 3 | 4 | 2 | 4 |
| 1-isopropyl-3-phenylurea | 4 | 9 | 9 | 8 | 5 | 10 | 5 | 9 | 10 | 10 | 10 | 3 | 3 |

TABLE II-continued

| Compounds of invention | Beet sugar | Bush bean | Wheat | Maize (Indian corn) | Common forage alfalfa | Echino-chloa | Set-aria | Poa | Digi-taria | Avena | Galium | Ama-rantus | Lam-ium |
|---|---|---|---|---|---|---|---|---|---|---|---|---|---|
| No treatment | 10 | 10 | 10 | 10 | 10 | 10 | 10 | 10 | 10 | 10 | 10 | 10 | 10 |

EXAMPLE 3

The plants listed below in Table 3 were treated in a hothouse in a postemergence application with the compounds listed in amounts of 1 kg of active agent per about 2.5 acres. The compounds were applied by spraying as aqueous suspensions in a uniform manner in amounts of 500 liter per about 2.5 acres.

Three weeks after application the compounds of the invention were found to have a higher activity and greater selectivity than the control compounds. The scale applied was the same as in Example 2.

TABLE III

| Compound of invention | Wheat | Maize | Common alfalfa | Echino-chloa | Setaria | Poa | Digi-taria | Avena | Galium | Amaran-thus | Lamium |
|---|---|---|---|---|---|---|---|---|---|---|---|
| 1-cyclopropyl-3-phenyl-urea | 10 | 10 | 10 | 0 | 0 | 0 | 5 | 0 | 0 | 0 | 0 |
| Control compound | | | | | | | | | | | |
| N-(3-chloro-4-methyl-phenyl)-N',N'-dimethyl-urea | 8 | 3 | 0 | 1 | 0 | 0 | 3 | 2 | 0 | 1 | 1 |
| 1-isopropyl-3-phenyl-urea | 10 | 10 | 6 | 5 | 2 | 10 | 10 | 8 | 5 | 1 | 1 |
| No treatment | 10 | 10 | 10 | 10 | 10 | 10 | 10 | 10 | 10 | 10 | 10 |

It is noted that all amounts given above for application of the compounds to the different plants were figured as liters per hectare. Since 1 hectare in the Anglo-Saxon system is 2.47 acres the amounts for convenience were stated as figured per about 2.5 acres in each case.

We claim:

1. A herbicidal composition comprising from about 10 to 80% by weight of a herbicidally active agent, and about 90 to 20% by weight of a relatively inert liquid or solid carrier material or a mixture of relatively inert liquid or solid carrier materials, said active agent being selected from the group consisting of 1-cyclopropyl-3-(3-fluorophenyl)-urea and 1-cyclopropyl-3-(3-trifluoromethylphenyl)-urea.

2. A composition as defined in claim 1 additionally comprising up to 20% by weight of a surface active agent or plurality of such agents.

3. A process for inhibition, termination or reduction of undesirable weed growth in plant cultures, comprising applying the composition of claim 1 to agricultural ground where said cultures are grown in an amount sufficient to provide between about 0.5 and 5 kg of active agent per hectare.

4. The compound 1-cyclopropyl-3-(3-fluorophenyl)-urea.

5. The compound 1-cyclopropyl-3-(3-trifluoromethylphenyl)-urea.

* * * * *